United States Patent [19]

Bartizal et al.

[11] Patent Number: 5,007,418

[45] Date of Patent: Apr. 16, 1991

[54] RESILIENT SEMI-RIGID ORTHOPEDIC SUPPORT DEVICES

[75] Inventors: Dennis C. Bartizal, Woodbury; Anthony J. Campagna, Roseville, both of Minn.

[73] Assignee: Minnesota Mining and Manufacturing Company, St. Paul, Minn.

[21] Appl. No.: 433,846

[22] Filed: Nov. 9, 1989

Related U.S. Application Data

[63] Continuation of Ser. No. 83,685, Aug. 7, 1987, Pat. No. 4,893,617, which is a continuation-in-part of Ser. No. 903,281, Sep. 3, 1986, Pat. No. 4,968,542.

[51] Int. Cl.$^5$ .............................................. A61F 5/04
[52] U.S. Cl. ................................... 128/90; 128/91 R
[58] Field of Search .................... 128/87 R, 90, 91 R, 128/878, 879, 155, 156, 157, 165, 85

[56] References Cited

U.S. PATENT DOCUMENTS

| | | | |
|---|---|---|---|
| 3,373,741 | 3/1965 | Hill et al. .............................. | 128/90 |
| 3,763,858 | 10/1973 | Buese ..................................... | 128/90 |
| 3,847,722 | 11/1974 | Kistner ................................. | 161/109 |
| 3,874,376 | 4/1975 | Dart et al. ............................ | 128/90 |
| 3,882,857 | 5/1975 | Woodall, Jr. .......................... | 128/90 |
| 4,134,397 | 1/1979 | Gianakakos et al. ................ | 128/90 |
| 4,235,228 | 11/1980 | Gaylord, Jr. et al. ............. | 128/91 R |
| 4,376,438 | 3/1983 | Straube et al. ....................... | 128/90 |
| 4,382,439 | 5/1983 | Shen ................................. | 128/89 R |
| 4,387,709 | 6/1983 | Shen ................................. | 128/89 R |
| 4,411,262 | 10/1983 | Von Bonin et al. .................. | 128/90 |
| 4,427,003 | 1/1984 | Fennimore et al. ................ | 128/90 |
| 4,433,680 | 2/1984 | Yoon ..................................... | 128/90 |
| 4,442,833 | 4/1984 | Dahlen ................................. | 128/90 |
| 4,502,479 | 3/1985 | Garwood et al. ...................... | 128/90 |
| 4,519,856 | 5/1985 | Lazzara ................................. | 156/49 |
| 4,537,184 | 8/1985 | Williams, Jr. ........................ | 128/90 |
| 4,598,826 | 7/1986 | Shinbach . | |
| 4,609,578 | 9/1986 | Reed ..................................... | 428/76 |
| 4,652,493 | 3/1987 | Reichmann .......................... | 128/90 |
| 4,667,661 | 5/1987 | Scholz et al. ........................ | 128/90 |
| 4,873,968 | 10/1989 | Finnieston ........................ | 128/89 R |

FOREIGN PATENT DOCUMENTS

54-100181 8/1979 Japan ................................. 94 A/237

OTHER PUBLICATIONS

J. A. Bradley, "The Modified Silicone Rubber Playing Cast", The Physician and Sportsmedicine, vol. 10, No. 12, Nov. 1982.

J. A. Bergfeld et al., "Soft Playing Splint for Protection of Significant Hand and Wrist Injuries in Sports", from the 48th Annual meeting of American Academy of Orthopaedic Surgeons, Las Vegas, Nev., Feb. 1981.

C. Henderson, "Cast Tips–Silicone (Sports) Cast Application", Online Communications, A Publication of the National Association of Orthopaedic Technologists, vol. 4, No. 6, Nov./Dec. 1986.

Electro Insulation Corporation product information and letter from same.

*Primary Examiner*—Robert A. Hafer
*Assistant Examiner*—Michael Brown
*Attorney, Agent, or Firm*—Donald M. Sell; Walter N. Kirn; Dale E. Hulse

[57] ABSTRACT

A curable orthopedic support material is disclosed wherein a flexible sheet material is impregnated with a liquid resin system; the resin-impregnated material cures upon exposure to a curing agent into a resilient, semi-rigid support device. In one preferred embodiment, one or more layers of a cushioning material such as foam is associated with the support material. The cured support is especially designed for orthopedic applications where conventional rigid casts are neither necessary not desirable, such as athletic uses.

23 Claims, No Drawings

RESILIENT SEMI-RIGID ORTHOPEDIC SUPPORT DEVICES

RELATED APPLICATIONS

This application is a continuation of copending application Ser. No. 07/083,685, filed Aug. 7, 1987, now U.S. Pat. No. 4,893,617, which is a continuation-in-part of copending application Ser. No. 903,281, filed Sept. 3, 1986 U.S. Pat. No. 4,968,542 entitled "Curable Material for Semi-Rigid Resilient Orthopedic Support," which application is incorporated herein by reference.

FIELD OF THE INVENTION

This invention relates broadly to the field of orthopedic support devices, including casts and splints and materials for their fabrication. It also relates to non-rigid supports such as elastic bandages and wraps.

BACKGROUND ART

Severe injury to body limbs, particularly injuries involving a fracture of the bone, are typically treated by immobilizing the injured limb in a rigid cast. Prior to about 1980, the vast majority of such rigid casts were made of plaster of Paris. Since about 1980, synthetic casting materials, particularly those comprising a knitted fiberglass fabric impregnated with a water activated polyurethane prepolymer resin system, have become quite popular. These polyurethane casting materials, like plaster of Paris bandages, are dipped in water, then wrapped around the injured limb or body part and shaped while the material is soft and pliable. The resin cures into a rigid immobilizing cast within a few minutes after application to the body.

Polyurethane casts offer numerous advantages over plaster of Paris, including a high strength-to-weight ratio, porosity, improved radiolucency, and water resistance. Because of these advantages, they are generally preferred, even though they are somewhat more expensive than plaster of Paris.

Plaster of Paris casts and known polyurethane casts, because of their rigidity, are often not suitable for treating injuries where total immobilization is not necessary and/or desirable, as for example, in the case of strains, sprains, and some minor fractures. These injuries are typically treated with a flexible type support such as tape or an elastic bandage, e.g., an "Ace" bandage, which is not impregnated with a hardening agent. Such supports offer various degrees of immobilization, and the support they provide is not necessarily stable and constant over time.

Furthermore, the rigid plaster of Paris and polyurethane casts of the prior art are unsuitable for use by athletes who choose to participate in athletic activities despite an injury. In such instances, the hardness and/or weightiness of such a prior art cast, if worn by the athlete, would present a safety hazard to all other participating athletes. Some athletes have sought to use support devices made of silicone rubber impregnated gauze as a means of protecting their injuries while reducing the safety hazard posed to the other participating athletes. However, such silicone rubber impregnated support devices still do not provide the degree of resiliency necessary to ensure safe usage, and in fact, the bulkiness and weightiness associated with silicone rubber often render the devices yet unsafe.

Thus, it would be a significant advancement in the art to provide a custom-fitted resilient support device which offers the stability of a cured cast without the rigidity and degree of immobilization attendant with currently available casting materials. Moreover, it would be another significant advancement in the art to provide such a resilient support device which can be worn by an athlete without posing significant safety risks to other participants. Such resilient support devices are disclosed and claimed herein.

SUMMARY OF THE INVENTION

The present invention provides a curable orthopedic support material comprising a flexible sheet material impregnated with a liquid resin which cures upon exposure to a curing agent into a semi-rigid, resilient support device having an "Immobilization Value" between about 45 and 400 pounds and a "Resiliency Value" of at least about 80 percent in the tests described hereinbelow. The support material further comprises packaging means for preventing contact of the resin with the curing agent prior to use. The invention also relates to the method of applying the support material and to the cured device formed from the support material.

In the preferred embodiment of the support material, a stretchy, knitted fabric, preferably polyester or fiberglass, is impregnated with a moisture-curing polyurethane prepolymer resin system (which cures to form a "resilient cured resin") wherein the theoretical isocyanate equivalent weight of the prepolymer is between about 500 and 5000 grams, the NCO:OH ratio is between about 1.5:1 and 5:1, and the average hydroxy equivalent weight of the polyol is at least about 400 grams, and preferably at least about 1000 grams. In one presently preferred embodiment, one or more layers of a cushioning material such as foam is associated with the support material upon application to provide more resiliency to the cured product. The support material is stored prior to use in a moisture impervious package such as that described in U.S. Pat. No. 4,598,826.

The cured support device provides stable semi-rigid support to the limb, allows some degree of movement, and has the ability to resume its original shape after deformation. It can be easily removed by cutting with scissors, or if the device is formed by wrapping a resin-impregnated tape around the limb, the support device can be removed by unwrapping.

The support materials of the invention are useful in a variety of orthopedic applications in both humans and animals, particularly as a semi-rigid support for sprains and minor fractures, or as a protective device to prevent injury. Both of these applications are especially useful in the field of sports medicine. In this regard, the resultant lightweight and resiliency of these support materials upon curing renders them safe for use by athletes. The support material may also be used as a secondary cast after primary healing of a fracture has occurred. Other applications include cast bracing where immobilization of the fracture area is required but movement in the proximate joint such as the elbow, knee, or ankle is desired.

DETAILED DESCRIPTION

The most preferred resins for use in the support materials of the present invention are moisture-curing polyurethane prepolymers prepared by the reaction of a polyol with an excess of polyisocyanate. The starting materials are from the same chemical classes as those used to form the rigid polyurethane casting materials well known in the art as described in U.S. Pat. Nos. 4,376,438, 4,433,680, and 4,502,479. However, the isocyanate equivalent weights of the prepolymers and the average hydroxy equivalent weight of the polyol must be modified to obtain the semi-rigid properties of the support materials of the present invention.

Additionally, other active hydrogen materials may be used alone or in conjunction with polyols to produce polymers which will be useful in this invention. Examples are primary and secondary amines, carboxylic acids, and thiols. When materials such as these are used, the overall equivalent weight of the active hydrogen components should be at least about 400 grams, and preferably at least about 1000 grams.

Suitable isocyanates are disclosed in the aforementioned patents. Those which are preferred include 2,4'-diphenylmethane diisocyanate, 4,4'-diphenylmethane diisocyanate, mixtures of these isomers together with possible small quantities of 2,2'-diphenylmethane diisocyanate (typical of commercially available diphenylmethane diisocyanate), and aromatic polyisocyanates and their mixtures such as are derived from phosgenation of the condensation product of aniline and formaldehyde. It is preferred to use an isocyanate which has low volatility such as diphenylmethane diisocyanate rather than a more volatile material such as toluene diisocyanate.

The degree of rigidity and resiliency in the cured support device is generally determined by the average hydroxy equivalent weight of the polYol or polYol blend. In general, the average hydroxy equivalent weight of the polyol or polyol blend will be greater than about 400 grams, and preferably greater than about 1000 grams in order to achieve the desired degree of semi-rigidity and resiliency. The choice of hydroxy equivalent weight is also dependent upon the molecular structure and type of the isocyanate as is well known. Suitable commercially available isocyanate starting materials include "Isonate" 143L (Dow Chemical), "Mondur" MRS (Mobay), and "PAPI" (Dow Chemical).

Typical polyols for use in the prepolymer resin system include polyalkylene ethers derived from the condensation of alkylene oxides (such as those available from Union Carbide under the tradename "Niax" and from BASF Wyandotte under the tradename "Pluracol"), polytetramethylene ether glycols (such as "Polymeg" from the Quaker Oats Co.), polycaprolactone polyols (such as the "Niax" PCP series of polyols from Union Carbide), and polyester polyols (hydroxyl-terminated polyesters obtained from esterification of dicarboxylic acids and diols) such as the "Lexorez" polyols available from Inolex Corp., Chemical Division.

An especially preferred resin for use in the support materials of the invention includes the isocyanate known as "Isonate" 143L available from Dow Chemical (a mixture of isocyanate compounds containing about 73% by weight of diphenylmethane diisocyanate) and a mixture of polypropylene oxide polyols available from Union Carbide as "Niax" LHT-28 and PPG 425. To prolong the shelf-life of the material, it is preferred to include about 0.02-0.1 percent by weight of benzoyl chloride and/or other suitable stabilizer (e.g., an antioxidant such as butylated hydroxy toluene at a level of about 0.05 to 0.25 weight percent).

Foaming of the resin which reduces the porosity of the cured device and its overall strength should be minimized. Foaming occurs because carbon dioxide is released when water reacts with isocyanate groups.

The most satisfactory method of minimizing foaming involves the addition of a foam suppresser such as silicone Antifoam A (Dow Corning), DB-100 silicone fluid (Dow Corning), or silicone surfactants L550 or L5303 (Union Carbide) to the resin. It is preferred to use a silicone liquid such as Dow Corning DB-100 at a concentration of about 0.1 to 1.0 percent by weight.

The isocyanates and the polyols are reacted with one another under conventional polyurethane reaction conditions known to those skilled in the art. The NCO:OH ratio of the reactants is in the range of about 1.5:1 to 7:1, and preferably between about 2.5:1 and 3.4:1. Where relatively high NCO:OH ratios are desired (e.g., 7:1), a plasticizer such as butyl benzyl phthalate, dibutyl phthalate, or dioctyl phthalate may be employed. The theoretical isocyanate equivalent weight of the prepolymer should be in the range of about 500 to 5000 grams, preferably between about 800 and 1200 grams, with the average hydroxy equivalent weight of the polyol being at least about 400 grams, and preferably at least about 1000 grams.

Other water-activated and alternative curing resins may be used to produce the curable support materials of the invention such as moisture-curing polyurea prepolymers, silane, epoxy, acrylate, polysulfide, and polyester functional materials. Light-curing materials such as certain active olefins e.g., acrylates, allylics, and pendant vinyls, are also candidates.

The resins used in the support materials of the invention tend to be more sticky than those used to form rigid casts. In order to improve handling characteristics, it is preferred to reduce the tack in accordance with one or more of the methods described in U.S. Pat. No. 4,667,661. The preferred method of detackifying the polyurethane prepolymer resin systems involves the addition of a lubricant, especially a surfactant, to the resin system. The preferred surfactants are block copolymers of propylene oxide and ethylene oxide in an amount ranging from about 3 to 6 percent by weight of the prepolymer system. Especially preferred are hydroxy functional polyethylene oxide terminated polypropylene oxides (sold under the tradename "Pluronic" by BASF Wyandotte).

The resin also preferably contains a catalyst to control the set time of the resin. To produce the cured support devices of the present invention, a cure time of about 3-18 minutes, preferably about 4-10 minutes following exposure to the curing agent, e.g., dipping in water, is preferred.

Suitable catalysts for moisture-curing polyisocyanate prepolymer resin systems are well known. Tertiary amine and catalysts such as 2,2'-dimorpholinodiethyl ether (DMDEE) described in U.S. Pat. No. 4,433,580 and 4-[2-[1-methyl-2-(4-morpholinyl)-ethoxy]ethyl]-morpholine (MEMPE) described in copending application Ser. No. 84,344 filed Oct. 4, 1985, in amounts ranging from about 1 to 3 percent by weight of the resin system, are useful for this purpose, with the MEMPE catalyst being especially preferred.

The flexible sheet material used in the support material of the present invention is preferably porous such that the sheet is at last partially impregnated with the resin. A porous sheet material also facilitates circulation of air through the cured device and evaporation of moisture from beneath the device. This contributes to the patient's comfort and to the maintenance of healthy skin under the device.

Examples of suitable flexible sheet materials include woven or knit fabrics comprised of natural or synthetic fibers such as polyamide, polyester, polyolefin, polyacrylamide, etc. Preferred sheet materials are extensible knit fabrics of fiberglass or polyester. Suitable extensible, heat-set fiberglass fabrics are disclosed in U.S. Pat. No. 4,609,578.

Sheet materials used in the orthopedic support materials of the present invention are generally long, narrow fabric strips (tapes) formed in rolls of various widths, from two inches to six inches wide. The fabric is impregnated with the curable resin in an amount of about 30 to 85 percent by weight of the resultant support material, and in the preferred embodiment, a fiberglass fabric is impregnated with enough resin such that the resin represents from about 40 to 60 percent by weight of the impregnated support material. The term "impregnate" is used to describe the condition in which the resin is thoroughly intermingled with and in surrounding relation to the threads or fibers of the fabric, and does not necessarily indicate that the resin is to any extent absorbed by the fibers themselves. Generally, the resin solution will flow into the capillary spaces between contiguous filaments of the fabric and will become bonded to the fabric upon curing.

The amount of resinous component applied to the fabric must be sufficient for the formation of a interlayer laminate bond, but not so much as to occlude the porosity and unnecessarily thicken the resin film which should be relatively thin for rapid and complete curing. Excessive resinous component may also cause the support material to be messy to handle due to stickiness or dripping of the resin.

The resin coated fabric strips in roll form are wound on a plastic core and sealed within a moisture and oxygen impermeable package. In the case of moisture-curing resins, the package is opened immediately before use and the roll is fully immersed in tap water for about 5 to 30 seconds. This is sufficient time for water to seep into the porous material and displace air. As long as the resin content is not so high as to cause the openings in the fabric to be filled with resin, more than enough water is absorbed by the roll in this manner. The roll may be squeezed underwater to replace entrapped air with water. When the roll is unwound during wrapping of the material, the excess moisture coats freshly exposed resin surfaces ensuring thorough wetting and rapid curing of the material. An alternate method comprises wrapping the material without dipping and then allowing atmospheric moisture or water provided by spraying or by application of a wet towel to cure the prepolymer.

Prior to applying the support material, protective padding is positioned about the limb of the patient. The padding may take the form of a tubular stockinet or some other convenient form, such as for example, an elongated strip or bandage which may be wrapped about the body member.

With the padding in proper position, the moistened support material is wrapped about the limb and over the protective padding in a manner similar to the application of an elastic-type bandage. The material is shaped in a manner similar to the shaping of a rigid synthetic or plaster cast.

Eight or fewer layers of the support material should be sufficient to form a cured device providing adequate support and/or immobilization for most applications. Removal of the cured device can generally be accomplished by applying moderate force to the exposed end of the fabric and delaminating the layers. This is a significant advantage over rigid casts which cannot be easily removed by the wearer and usually require power tools such as a saw for removal. The cured devices of the present invention can also be removed with scissors.

The cured semi-rigid support devices of the present invention are characterized by their flexibility and resiliency as compared to conventional rigid casts formed of synthetic resins or plaster of Paris. They offer more rigidity however than elastic support bandages and wraps which are not impregnated with a curable resin. They also provide greater support and immobilization.

To measure the degree of immobilization provided by the finished casts of the invention, the following test was devised.

Immobilization Test

The test involves applying a force to a sample of cured support material which has been wrapped around a solid cylindrical-shaped article designed to simulate a body limb. The cured sample is subjected to a bending force at a given rate of speed to a given total deflection.

The solid cylinder used as the simulated limb is made using a urethane hydrogel prepolymer marketed by the AC&S Division of 3M as Chemical Grout 5620 (and is described in U.S. Pat. No. 4,315,703 as "Propolymer A"). This material is compounded with clay and water to produce the cylinder. The formulation is as follows:
145 g Chemical Grout 5620
80 g Bentonite Clay (Federal Bentonite, Div. of Aurora Industries, Montgomery, Ill.)
600 g Water The water and clay are premixed, and the prepolymer is added under constant agitation for 10-20 seconds. The mixture is poured into a cylindrical mold which is lined with polyethylene for release. The set time is about 45 seconds from the introduction of the prepolymer into the water. The cylinder has a diameter of 6.0 cm and a length of 30.5 cm. After curing for 24 hours at 22°-25° C., the cylinder is stored in a moist polyethylene bag and refrigerated to prevent shrinkage.

When water curable support materials are tested, they are immersed as a 4-yard (3.65 m) roll in water for about 20 seconds and wrapped around the cylinder spirally so as to provide a total of four layers over a length of 3-25 cm of the cylinder. Stockinet is normally used to cover the cylinder before applying the tape.

Support material is applied to a cylinder which has been conditioned at room temperature for 2-4 hours. The support material is allowed to cure for 1 hour at ambient conditions, and the system is replaced in the refrigerator at 2°-5° C. for 18-24 hours before being removed for additional ambient conditioning of 2-4 hours. The test is then performed.

The test equipment is an Instron Tensile Tester Model 1122 set up with a 2-1000 pound (0.9-453 kg) full-scale load cell and a variable speed chart. The cylinder wrapped with the test sample is placed on a sample holder designed specifically to fit into the Instron test equipment to perform a three point bend test. The equipment consists of two parts, a base member and an upper member which are mounted on the Instron. The base member consists of a ¾-inch (1.9 cm) aluminum plate 13 inches (33 cm) long and 8¼ inches (20.95 cm) wide. Mounted along the top side of the plate, perpendicular to the lengthwise axis of the plate are two rectangular aluminum supports which are one-inch (2.54 cm) thick, 3 inches (7.62 cm) high and 5¼ inches (13.3 cm) long. The supports are located respectively, 5 inches (12.7 cm) from the ends of the plate, as measured to the center of the support. Each support is mounted 1.5 inches (3.81 cm) from each side edge of the plate. The supports are exactly 3 inches (7.62 cm) apart from each other. Bonded to the top of each support along its length is ¾ inch (1.9 cm) diameter aluminum rod stock upon which the test sample is placed. The rods on each support are 3 inches (7.62 cm) apart from center to center. This entire structure serves as the base member providing two points of the three point bend test. The base member is bolted to the base of the Instron and remains stationary during the test. The upper member of the test equipment consists of a one-inch (2.54 cm) thick piece of aluminum which is 5¼ inches (13.3 cm) long by 2⅞ inches (7.3 cm) high, i.e., similar in size and shape to the supports on the lower member. A stainless steel cylindrical chuck which is 1½ inches (3.81 cm) in diameter and 1¾ inches (4.4 cm) high threaded at 13 threads to the inch is fixed to the aluminum piece and is used to mount it onto the Instron. A ¾ inch (1.9 cm) diameter aluminum rod 5¼ inches (13.3 cm) long is bonded to the bottom edge of the aluminum piece along its length and provides the third point of contact in the test such that the sample is bent between the two parallel lower supports and the aluminum piece on the upper member, which is also parallel to the lower supports. When fixed to the Instron, the upper member lowers at a given rate of speed and comes in contact with the test sample.

The test sample (which is centered on the simulated limb) is centered on and perpendicular to the two supports of the base member of the test device. The aluminum piece of the top member is allowed to contact the sample at its center at a rate of 1 inch (2.54 cm)/minute to a total deflection of one inch. The settings used on the Instron for full scale load and chart speed are dependent on the rigidity of the particular sample and the sensitivity desired in the measurement, as is known to those skilled in the art.

The test result is taken as that force which results from the resistance imparted by the sample at the maximum deflection point of one-inch. The force reading ("Immobilization Value") is taken directly off the chart.

There is a large difference observed in this test between the Immobilization Values obtained when nonresin-impregnated elastic bandages and rigid-forming cast materials are tested. Generally, the unwrapped support device has an Immobilization Value of about 20 pounds (9 kg). Elastic bandage materials such as an Ace L; bandage have Immobilization Values of 30–40 pounds (13.6–18.1 kg), depending on the number of rolls. rigid casts such as those formed from Scotchcast 2 Casting Tape (3M) typically have Immobilization Values in the range of about 500–700 pounds (226.5–317.1 kg). In contrast, cured support devices of the present invention have Immobilization Values of about 45–400 pounds (22.6–181.2 kg), preferably about 80–200 pounds (36.2–90.6 kg).

Resiliency Test

To measure the resiliency of the cured support materials of the present invention, the following Resiliency Test was devised:

The test samples are produced by wrapping the resin-coated tape, which has been activated by water immersion, around a mandrel which has an outside diameter of 5 cm. The mandrel is covered with 2 inch (5.1 cm) stockinet material before wrapping. The sample is wrapped to form six layers of material in a cylindrical shape. The samples are allowed to set at least 24 hours at room temperature before testing.

The test equipment is a Chatillon model USTE tester equipped with a support platen on the bottom and a knife edge platen on the top.

The test is done by measuring the outside diameter of the cured sample followed by placing the sample in the test equipment. The sample is laid lengthwise (parallel to the knife edge) in the tester and the force is applied. The sample is deformed such that the inside surface comes into contact with the opposite wall. The force is removed and the diameter is remeasured with a caliper. The percent recovery ("Resiliency Value") is calculated using the two diameter measurements.

For rigid casts such as those formed from Scotchcast 2, the Resiliency Value is essentially zero. Rigid casts containing a knit polyester sheet material generally show greater resiliency. Cured support devices of the present invention have a Resiliency Value of at least about 80 percent, and preferably, from about 90 to 100 percent.

The invention is further illustrated by the following non-limiting examples.

EXAMPLE 1

To 757.38 g of "Isonate" 143L (UpJohn) were added 1.85 g of benzoyl chloride, 6.6 g of DB-100 (antifoaming agent available from Dow Chemical), and 17.80 g of "Ionol" (butylated hydroxytoluene available from Shell Chemical Co.). After allowing these ingredients to mix at ambient temperature for 10 minutes, 2602.45 g of "Niax" LHT-28 (polyol available from Union Carbide), 112.32 g of "Niax" PPG-425 (polyol available from Union Carbide), 112.32 g of "Niax" PPG-425 (polyol available from Union Carbide), 55.62 g of MEMPE catalyst (described in copending application Ser. No. 784,344, filed Oct. 4, 1985), and 145.90 g of "Pluronic" F-108 (surfactant available from BASF Wyandotte) were added sequentially. The reaction mixture was heated to 60° C. and held for 3 hours. After cooling, a sample was taken which had a viscosity of 30,000 cps, a measured isocyanate equivalent weight of 1280 grams, an average hydroxy equivalent weight of 1536 grams, and an NCO:OH ratio of 2.8:1.

The resin was coated onto various fabrics including fiberglass, polyester knit, and "Ace" bandage fabric. Each material has a different capacity for resin absorption which necessitated different coating weights to achieve good lamination of the layers in the final cured device. The fiberglass resin-impregnated material was 45% resin. The polyester knit resin-impregnated material was 55% resin. The "Ace" bandage resin-impregnated material was 60% resin. All of the samples, with the exception of the Ace material, were stable. The "Ace" material began to react with the resin very quickly, indicating that a considerable amount of water was present.

EXAMPLE 2

A moisture-curing, silane-based support material was made by dissolving a commercially available reactive liquid silicone rubber compound, Dow Corning "Silastic" 732 RTV, in toluene to 70% solids. The solution was coated onto a 3-inch (7.62 cm) wide fiberglass knit fabric of the type used in "Scotchcast" 2 Casting Tape (3M) described in U.S. Pat. No. 4,609,578 to 45% resin solids, and packaged in a moisture impermeable package. After being removed from the package, it was allowed to cure with ambient moisture.

EXAMPLE 3

To 1631.48 g of "Isonate" 143L were added 1.85 g of benzoyl chloride, 6.66 g of DB-100, and 17.76 g of butylated hydroxytoluene. After allowing these ingredients to mix together at ambient temperature for 10 minutes, 1986 g of "Niax" PPG-1025 (polypropylene oxide diol available from Union Carbide) and 55.5 g of MEMPE catalyst were added. The reaction mixture was heated to 60° C. and held for 3 hours. After cooling, a sample was taken which had a measured viscosity of 443,000 cps, a measured isocyanate equivalent weight of 544 grams, an average hydroxy equivalent weight Of 491 grams, and an NCO:OH ratio of 2.8:1. This resin was coated onto knitted fiberglass fabric as described in Example 2 at 45% resin content.

EXAMPLE 4

To 542.85 g of "Isonate" 143L were added 1.85 g of benzoyl chloride, 66.6 g of DB-100, and 17.76 g of butylated hydroxytoluene. The materials were allowed to mix at ambient temperature for 10 minutes. To the mixture were added 3075.38 g of PPG-3025 (a polypropylene oxide diol available from Union Carbide) and 55.5 g of MEMPE catalyst. The reaction mixture was heated to 60° C. and held for 3 hours. After cooling, a sample was taken that had a measured viscosity of 38,500 cps, a measured isocyanate equivalent weight of 2325 grams, an average hydroxy equivalent weight of 1550 grams, and an NCO:OH ratio of 1.90:1. The resin was coated onto knitted fiberglass fabric as described in Example 2 at 45% resin content.

EXAMPLE 5

To 314.67 g of "Isonate" 143L were added 1.75 g of benzoyl chloride, 6.30 g of DB-100, and 16.80 g of "Ionol". After allowing the ingredients to mix at ambient temperature for 10 minutes, 2897.98 g of LHT-28, 210.0 g of "Pluronic" F-108, and 52.5 g of MEMPE catalyst were added sequentially. The reaction mixture was heated to 70° C. and held for three hours. After cooling, a sample was taken which had a viscosity of 210,000 cps, an average hydroxy equivalent weight of 2102.89 g, and a measured isocyanate equivalent weight of 5130 g. The resin was coated onto a knitted fiberglass fabric as described in Example 2 at 45% resin content.

EXAMPLE 6

To 724.66 g of "Isonate" 143L were added 1.66 g of benzoyl chloride, 5.94 g of DB-100, and 15.84 g of butylated hydroxytoluene. The materials were allowed to mix at ambient temperature for 10 minutes. To the mixture were added 2247.33 g of PPG-3025 (polypropylene oxide diol available from Union Carbide) and 42.90 g of MEMPE catalyst. The reaction mixture was heated to 60° C. and held for 2 hours. At this point, 261.69 g of Jeffamine ED-2001 (an amino functional polyoxyethylene ether from Texaco) was added very slowly with good agitation. The material was held an additional ½ hour and allowed to cool. The resultant material was a resin having a viscosity of 240,000 cps and a measured isocyanate equivalent weight of 1157 g. The resin was coated onto knitted fiberglass fabric as described in Example 2 at 45% resin content.

EXAMPLE 7

To 366.11 g of "Isonate" 143L were added 1.75 g of benzoyl chloride, 6.3 g of DB-100, and 16.80 g of "Ionol". After allowing the ingredients to mix for 10 minute at ambient temperature, 2848.2 g of LHT-28, 208.33 g of "Pluronic" F-108, and 52.51 g of MEMPE catalyst were added sequentially. The reaction mixture was heated to 70° C. and held for 3 hours. After cooling, a sample was taken which had a viscosity of 134,000 cps, an average hydroxy equivalent weight of 2103.84 g, and a measured isocyanate equivalent weight of 4085 g. The resin was coated onto a knitted fiberglass fabric as described in Example 2 at 45% resin content.

Preferred Embodiments of the Present Invention Employing A Cushioning Material In some presently preferred embodiments of the present invention, a layer of cushioning material, such as foam, may be associated with the resin-impregnated flexible sheet material in order to provide an orthopedic support device having greater resiliency and lightweight for the bulk provided. In these preferred embodiments, the resin-impregnated flexible sheet materials are prepared in accordance with the disclosure set forth hereinabove. The cushioning layer or foam is then associated with the resin-impregnated sheet material upon application to the body part, as will be explained in more detail hereinafter.

The cushioning layer, when used in conjunction with the resin-impregnated flexible sheet material, provides a finished orthopedic support device which is semi-rigid and very resilient, and is particularly suitable as an athletic protection device. Although various materials may be used as the cushioning layer, foam is the presently most preferred material. However, materials such as flexible resilient felts, water laid sheets, air laid or carded sheets and the like could also be used to form a cushioning layer in accordance with the present invention.

With the most important characteristic being the cushioning nature of the foam layer, other characteristics of the foam are of less importance. Thus, either an open-celled or a closed-celled foam may be employed. However, it is preferable that the foam sheet employed be an open-celled foam having sufficient porosity to allow adequate moisture vapor transmission therethrough. In this regard, the preferred open-celled foams sheets preferably have a porosity of at least about 1625 milligrams of water vapor per square meter per hour (1625 mg $H_2O/m^2$-hr) This can be achieved using an open-celled foam having from about 10 to about 120 pores per inch. As used herein, the term "pores per inch" refers to the average number of pores located along a linear inch of the foam sheet. The number of pores per linear inch may be determined, for example, by measuring the foam's resistance to air flow or a pressure differential and using such information to calculate the approximate number of pores in the foam.

Furthermore, foam sheet thicknesses of between about ⅛ inch and about ¾ inch are presently preferred, with foam sheet thicknesses of about ¼ inch to about ½ inch being most presently preferred. Foam sheets having thicknesses much less than this are generally too thin to provide the cushioning protection desired. Foam sheets with thicknesses greater than this tend to provide an orthopedic support material which is too bulky and cumbersome and which may not have adequate porosity.

Preferably, the foam layer has an adhesive applied on one side thereof to assist in the proper positioning of the foam layer during application. One presently preferred foam material having such an adhesive on one side thereof is available from 3M Company, St. Paul, Minn. as Reston TM brand self adhering foam pad.

As mentioned, presently preferred sheet materials for use in the present invention include the extensible, heat-set fiberglass fabrics which are disclosed in U.S. Pat. No. 4,609,578. Another presently preferred sheet material is a somewhat less extensible, heat-set fiberglass fabric which is knitted in a fashion identical to the fiberglass fabrics of U.S. Pat. No. 4,609,578, with the exception that only every other needle of the knitting apparatus is threaded, thereby providing a thinner and more open fabric.

The method of forming an orthopedic support device using a layer of foam or other cushioning material will now be explained. The resin-impregnated flexible sheet materials are prepared and sealed in moisture impermeable packages in the manner explained previously. The foam sheet remains separate from the packaged resin-impregnated material, and is cut to the dimensions of the body part to be immobilized.

To apply the support device, a protective padding such as a stockinet is first positioned about the body part to be immobilized. Next, the layer of foam material (which has been cut to the appropriate size) is applied around the stockinet such that the adhesive side of the foam layer adheres to the stockinet.

The package containing the resin-impregnated support material is opened, and the roll of resin-impregnated material is fully immersed in tap water for about 5 to 30 seconds to activate the resin. If desired, the roll may be squeezed under water to replace entrapped air with water.

After activation of the resin, the resin-impregnated support material is wrapped around the foam layer as tightly as is needed to provide the degree of support and/or immobilization desired. Enough layers of the resin-impregnated support material are wrapped around the foam layer to form a cured device which will provide such degree of support and/or immobilization.

If desired, additional protection may be provided by applying a second layer of foam and a second wrap of resin-impregnated support material so as to provide a multiple layered orthopedic support device having an exceptional amount of flexibility, and even greater immobilization characteristics. To achieve this, a second layer of the foam material is applied around the previously applied wrap of resin-impregnated support material such that the adhesive side of the foam layer adheres to the resin-impregnated material. Subsequently, another roll of the resin-impregnated support material is activated by dipping in water, and is wrapped around the second layer of foam in the same fashion as with the first roll of resin-impregnated material.

Preferably, the second roll of resin-impregnated material is wrapped around the second layer of foam only as manY times as are needed to secure the second layer of foam in place and protect it from destructive wear or abrasion. In this manner, the first wrap of resin-impregnated material serves primarily to provide the degree of support and/or immobilization necessary, while the second wrap of resin-impregnated material (which is preferably in fewer layers) serves primarily to secure the second layer of foam in place. The first and second layers of foam, in conjunction with the resilient nature of the cured resin, serve to provide an orthopedic support device having exceptional resiliency which is safe for use by athletes who engage in contact sports.

It is presently most preferable to form an orthopedic support device comprising successive layers of: (1) stockinet, (2) foam, (3) resin-impregnated material, (4) second layer of foam, (5) second wrap of resin-impregnated material, as described hereinabove. However, it will be understood that any number of layers of foam and/or resin-impregnated material may be used to provide the degree of immobilization and/or resiliency required for different applications of the present invention. Thus, multiple layers of foam may be used between successive wraps of resin-impregnated material, or conversely, several wraps of resin-impregnated material may be used between successive layers of foam.

A few non-limiting examples are given below in order to illustrate how the present invention may be practiced using one or more layers of foam material.

EXAMPLE 8

In this example, a moisture curable resin was prepared for use in the other examples. First, about 566 grams of Isonate 143L (Upjohn), about 1.5 grams of benzoyl chloride, about 5.4 grams of DB-100 antifoaming agent (Dow Chemical), and about 14.4 grams of Ionol butylated hydroxytoluene (Shell Chemical Co.) were mixed together. After continuous mixing for about 10 minutes at room temperature, the following ingredients were added sequentially to the mixture: about 120 grams of Pluronic F-108 (available from BASF Wyandotte), about 2203 grams of LHT34 (Union Carbide), and about 90 grams of MEMPE catalyst (described in copending patent application Ser. No. 784,344, filed Oct. 4, 1985). The reaction mixture was then heated to 60° C. under a nitrogen atmosphere, and was allowed to react for about 3 hours.

The resultant resin of this Example 8 had a viscosity of about 66,000 centipoise (cp), a measured isocyanate equivalent weight of about 3540 grams, an average hydroxy equivalent weight of about 1773 grams, and an NCO:OH ratio of about 3.0:1. After cooling to room temperature, this resin was used to coat the fabric in each of Examples 9 and 10 below.

EXAMPLE 9

In this example, a curable orthopedic support material was prepared by coating the curable resin of Example 8 onto strips of two-inch wide and three-inch wide fiberglass knit fabric made in accordance with the Example of U.S. Pat. No. 4,609,578. This fiberglass knit fabric had at least 20% stretch along its length. Coating of the resin onto the fabric strips was done in a very low humidity environment (2.5% relative humidity) such that the resin represented about 45% by weight of the resin-impregnated material. After coating, the resin-impregnated material was wound onto plastic cores into twelve foot lengths, and each roll of material was packaged in a moisture impervious pouch to await further use. When tested in accordance with the Immobilization and Resiliency Tests set forth herein, the material of this Example 9 was determined to have an Immobilization Value of about 56 pounds (25.4 kg) and a Resiliency Value of about 97%.

EXAMPLE 10

In this example, a curable orthopedic support material was prepared by coating the curable resin of Example 8 onto strips of two-inch wide and three-inch wide fiberglass knit fabric which was made in accordance with the Example in U.S. Pat. No. 4,609,578, with the exception that only every other needle of the knitting apparatus was threaded, thereby providing a thinner and more open fabric. The resultant fabric had 6 wales per inch and 15 courses per inch. This fabric was wound with tension and heat-set, giving it a resultant longitudinal stretch of about 10% to 12%. The fabric was then coated in a very low humidity environment (2.5% relative humidity) with enough of the resin from Example 8 to provide a resin-impregnated material having 45% resin by weight. After coating, the resin-impregnated material was wound onto plastic cores into 12 foot lengths, and each roll was packaged in a moisture impervious pouch to await further use. When tested in accordance with the Immobilization and Resiliency Tests set forth herein, the material of this Example 10 was determined to have an Immobilization Value of about 45 pounds (20.4 kg) and a Resiliency Value of about 97%. The material of this Example 10 is particularly suitable to form the outerwrap or last few layers of the othropedic support devices of the present invention.

EXAMPLE 11

In this example, a resilient and semi-rigid orthopedic support device, particularly suitable as an athletic protection device, was prepared as follows. First, a length of two inch diameter rib knit polyester stockinet was placed over a human forearm from the elbow down to the distal palmar area. Next, a layer of foam (dimensioned to fit the forearm), having a thickness of 3/16 inch and having a pressure-sensitive adhesive coated on one side thereof, was applied around the stockinet by pressing the adhesive side of the foam against the stockinet. The foam used was Reston TM brand self adhering foam pad available from 3M Company.

Next, a roll of resin-impregnated orthopedic support material prepared in accordance with Example 9 was removed from its protective pouch and dipped in water to initiate cure. This roll, which was three inches wide and twelve feet long, was then wrapped spirally around the layer of foam. Moments afterwards, an additional layer of the 3/16 inch thick Reston TM brand foam (which had been cut to fit) was adhered to the wrap of resin-impregnated support material by pressing the adhesive side of the foam against the resin-impregnated support material. Finally, an additional wrap of the resin-impregnated support material was applied around the second layer of foam. This second wrap of resin-impregnated material was formed from a second roll of the material prepared in accordance with Example 9 having a width of two inches and a length of twelve feet. After activation of the resin by dipping in water, this second roll was wrapped around the second layer of foam until about two layers of the material had been applied over the entire foam surface. The second roll of material was then cut, and the remainder of the material was discarded.

The orthopedic support device so formed was then allowed to cure for about 30 minutes. After curing, the orthopedic support device exhibited a good degree of immobilization and provided good protection to the arm to which it was applied. At the same time, the finished support device was very soft to the touch, lightweight, and resilient, and was considered safe for use by an athlete in contact sports.

EXAMPLE 12

In this example, an orthopedic support device was formed in identical fashion to Example 11, except that a roll of the resin-impregnated material of Example 10 was used to form the second or outer wrap around the second layer of foam. (However, as in Example 11, a roll of material of Example 9 was used to form the first wrap around the first layer of foam.) Since the resin-impregnated support material of Example 10 is somewhat thinner than that of Example 9, an even softer exterior was provided in the final product of this Example 12.

Again, it was noted that good immobilization of the forearm had been achieved, and that the resilient support material and compressible foam provided a safe, cushioned device which could be safely used by athletic participants.

EXAMPLE 13

In this example, a moisture curable resin was prepared in accordance with the procedure of Example 8, except that the following ingredients and amounts were employed: 519 grams of Isonate 143L, 1 gram of benzoyl chloride, 3.6 grams of DB-100 antifoaming agent, 9.6 grams of Ionol butylated hydroxytoluene, 80 grams of Pluronic F-108, 1007 grams of LHT-28 (Union Carbide), and 80 grams of MEMPE catalyst. The procedure of Example 8 was further modified by heating the reaction mixture to about 70° C. under a nitrogen atmosphere for about 12 hours, adding 300 grams of butyl benzyl phthalate to the mixture, and then allowing the mixture to cool to room temperature.

The resultant resin of this Example 13 had a viscosity of about 9,800 centipoise, a measured isocyanate equivalent weight of about 1251 grams, an average hydroxy equivalent weight of about 2113 grams, and an NCO:OH ratio of about 7.0:1. This resin was used to coat the fabric in Example 14 below.

EXAMPLE 14

In this example, a curable orthopedic support material was prepared in accordance with Example 9, with the sole exception that the resin of Example 13 was used to coat the fiberglass knit fabric strips which were three inches wide. When tested in accordance with the Immobilization and Resiliency Tests set forth herein, the material of this Example 14 was determined to have an Immobilization Value of about 55 pounds (25.0 kg) and a Resiliency Value of about 95%.

The orthopedic support materials of Examples 1-7, 9-10, and 14 were compared with both rigid casts and conventional nonresin-impregnated elastic bandages and wraps of the prior art in the Immobilization and Resiliency Tests described above. The results are given in the following Table I.

TABLE I

| Test Sample | NCO Eq.wt. | Immobilization Value lbs. (kg) | Resiliency Value (%) |
|---|---|---|---|
| Control Cylinder | N.A. | 21.5 (9.74 kg) | N.A. |
| Ace Wrap[1] (1 roll) uncoated | N.A. | 30.0 (13.59 kg) | 0–5 |

TABLE I-continued

| Test Sample | NCO Eq.wt. | Immobilization Value lbs. (kg) | | Resiliency Value (%) |
|---|---|---|---|---|
| Dr. Scholl's[2] Tape (5 layers) uncoated | N.A. | 58.0 (26.27 kg) | With Stockinet | 0 |
|  |  | 62.0 (28.08 kg) | No Stockinet | 0 |
| "Coban" Tape (5 layers) uncoated | N.A. | 42.0 (19.02 kg) |  | 0-5 |
| "Scotchcast" 2 Casting Tape | 375 | 549.0 (248.69 kg) |  | 0-5 |
| "Scotchcast" Plus Casting Tape | 340 | 628.0 (284.48 kg) |  | 0-5 |
| CutterCast ®[3] Casting Tape (3-inch) | Unknown | 165 (74.74 kg) |  | 73.0 |
| Example 1 (Fabric as in Example 2) | 1280 | 95.0 (43.03 kg) |  | 98.0 |
| Example 2 |  | 74.0 (33.52 kg) |  | 99.1 |
| Example 3 | 544 | 210.0 (95.13 kg) |  | 93.5 |
| Example 4 | 2325 | 70.0 (31.71 kg) |  | 91.9 |
| Example 5 | 5069 | 49.0 (22.19 kg) |  | 85.0 |
| Example 6 | 1157 | 58.0 (26.27 kg) |  | 94.0 |
| Example 7 | 4085 | 64.0 (28.99 kg) |  | 93.0 |
| Example 9 | 3540 | 56 (25.4 kg) |  | 97.0 |
| Example 10 | 3540 | 45 (20.4 kg) |  | 97.0 |
| Example 14 | 1251 | 55 (25.0 kg) |  | 95.0 |

[1]"Ace" brand Spandex Elastic Bandage, Becton Dickinson, 3 inches (7.62 cm) wide and 2 yards (1.82 cm) long (unstretched)
[2]Scholl's Inc., Memphis, Tenn.
[3]Cutter Biomedical, Berkeley, California The present invention may be embodied in other specific forms without departing from its spirit or essential characteristics. The described embodiments are to be considered in all respects only as illustrative and not restrictive. The scope of the invention is, therefore, indicated by the appended claims rather by the foregoing description. All changes which come within the meaning and range of equivalency of the claims are to be embraced within their scope.

What is claimed and desired to be secured by United States Letters Patent is:

1. An orthopedic support material, comprising:
   a flexible sheet material impregnated with a curable resin which cures upon exposure to a curing agent into a resilient and semi-rigid state having an Immobilization Value between about 45 pounds and about 400 pounds and a Resiliency Value of at least about 80 percent; and
   a layer of cushioning material adjacent said resin-impregnated flexible sheet material.

2. An orthopedic support material as defined in claim 1 wherein said cushioning material is foam.

3. An orthopedic support material as defined in claim 2 wherein said foam is an open-celled foam having a porosity of at least about 1625 mg $H_2O/m^2$-hr.

4. An orthopedic support material as defined in claim 2 wherein said foam has from about 10 to about 120 pores per inch.

5. An orthopedic support material as defined in claim 2 wherein said foam is from about 1/8 inch to about ¾ inch thick.

6. An orthopedic support material as defined in claim 2 wherein said foam has an adhesive applied to one side thereof.

7. An orthopedic support material as defined in claim 1 wherein said resin comprises a moisture-curing isocyanate-functional prepolymer formed by the reaction of a polyfunctional active hydrogen-containing component with an excess of polyisocyanate component.

8. An orthopedic support material as defined in claim 7 wherein the isocyanate equivalent weight of said resin is between about 500 and about 5000 grams.

9. An orthopedic support material as defined in claim 7 wherein the isocyanate equivalent weight of said resin is between about 800 and about 1200 grams.

10. An orthopedic support material as defined in claim 7 wherein said polyfunctional active hydrogen-containing component is a polyol.

11. An orthopedic support material as defined in claim 10 wherein the average hydroxy equivalent weight of said polyol is at least about 400 grams.

12. An orthopedic support material as defined in claim 10 wherein the average hydroxy equivalent weight of said polyol is at least about 1000 grams.

13. An orthopedic support material as defined in claim 7 wherein said resin has an NCO:OH ratio of from about 1.5:1 to about 7:1.

14. An orthopedic support material as defined in claim 7 wherein said resin has an NCO:OH ratio of from about 2.5:1 to about 3.4:1.

15. An orthopedic support material as defined in claim 1 wherein said flexible sheet material is a knitted fabric made of fibers selected from the group consisting of fiberglass, polyolefin, polyamide, polyester, polyaramide, and mixtures thereof.

16. An orthopedic support material as defined in claim 15 wherein said flexible sheet material is a fiberglass knit having an extensibility of at least about 20 percent in the lengthwise direction.

17. An orthopedic support material as defined in claim 1 wherein said resin further comprises a lubricant to reduce the tackiness of the resin during application.

18. An orthopedic support material as defined in claim 17 wherein said lubricant is a surfactant.

19. An orthopedic support material as defined in claim 18 wherein said surfactant is a block copolymer of propylene oxide and ethylene oxide.

20. An orthopedic support material as defined in claim 7 wherein said resin-impregnated flexible sheet material is packaged in a moisture proof container prior to use.

21. An orthopedic support material as defined in claim 1 wherein said resin-impregnated flexible sheet material cures upon exposure to a curing agent into a resilient and semi-rigid state having an Immobilizing Value between about 80 pounds and about 200 pounds and a Resiliency Value of at least about 90 percent.

22. An orthopedic support device, comprising:
   a first layer of cushioning material for positioning around a body part;
   one or more layers of a first flexible sheet material for positioning around said first layer of cushioning material, said first flexible sheet material being impregnated with a curable resin which cures upon exposure to a curing agent into a resilient and semi-rigid state having an Immobilization Value between about 45 pounds and about 400 pounds and a Resiliency Value of at least about 80 percent;
   a second layer of cushioning material for positioning around said flexible sheet material; and
   one or more layers of a second flexible sheet material for positioning around said second layer of cushioning material, said second flexible sheet material also being impregnated with said curable resin.

23. An orthopedic support device as defined in claim 22 wherein said first and second layers of cushioning material comprise foam.

* * * * *

UNITED STATES PATENT AND TRADEMARK OFFICE
CERTIFICATE OF CORRECTION

PATENT NO. : 5,007,418

DATED : April 16, 1991

INVENTOR(S) : Dennis C. Bartizal et al.

It is certified that error appears in the above-identified patent and that said Letters Patent is hereby corrected as shown below:

Title Page:
Abstract, last line, "not" should be --nor--.

Col. 1, line 10, "U.S. Pat. No. 4,968,542" should be --, now U.S. Pat. No. 4,968,542,--.

Col. 3, line 31, "polYol or polYol" should be --polyol or polyol--.

Col. 4, line 59, "34,344" should be --784,344,--.

Col. 6, line 49, "3-25" should be --23-25--.

Col. 7, line 54, delete "L;".

Col. 7, line 56, "rigid" should be --Rigid--.

Col. 9, line 20, "Of" should be --of--.

Col. 11, line 64, "manY" should be --many--.

Col. 13, line 27, "othropedic" should be --orthopedic--.

Col. 16, line 46, "Immobilizing" should be --Immobilization--.

Col. 16, line 60, insert --first-- before "flexible".

Signed and Sealed this

Twenty-seventh Day of October, 1992

Attest:

DOUGLAS B. COMER

*Attesting Officer*   *Acting Commissioner of Patents and Trademarks*